US00PP12827P2

(12) United States Plant Patent
Guillou et al.

(10) Patent No.: US PP12,827 P2
(45) Date of Patent: Aug. 6, 2002

(54) GERANIUM PLANT NAMED 'GUIPIERRE'

(75) Inventors: Bernard Guillou; Jacques Guillou; Maurice Guillou, all of St. Malo (FR)

(73) Assignee: Ets. Guillou Freres, St. Malo (FR)

( * ) Notice: Subject to any disclaimer, the term of this patent is extended or adjusted under 35 U.S.C. 154(b) by 0 days.

(21) Appl. No.: 09/320,927

(22) Filed: May 27, 1999

(51) Int. Cl.[7] ..... A01H 5/00
(52) U.S. Cl. ..... Plt./332

(58) Field of Search ..... Plt./332

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Geranium plant named 'Guipierre', characterized by its upright plant habit; moderately vigorous growth habit; zoned dark green leaves; numerous long-lasting dark purplish red-colored semi-double to double flowers; basal branching; high yield of cuttings; continuous flowering throughout the summer; and foliage tolerant to rain, wind and stress conditions.

2 Drawing Sheets

BACKGROUND OF THE INVENTION

The present invention relates to a new and distinct cultivar of Geranium plant, botanically known as *Pelargonium peltatum*, and hereinafter referred to by the cultivar name Guipierre.

The new Geranium is a product of a planned breeding program conducted by the Inventors in St. Malo, France. The objective of the breeding program was to develop new cultivars with interesting and unique flower colors.

The new Geranium originated from a cross made by the Inventors of the *Pelargonium peltatum* cultivar Jacques Cartier, not patented, as the male, or pollen parent, with the proprietary *Pelargonium peltatum* selection code number 4384, as the female, or seed, parent in 1989. The cultivar Guipierre was discovered and selected by the Inventors as a flowering plant within the progeny of the stated cross in a controlled environment in St. Malo, France, in 1989.

Asexual reproduction of the new cultivar by terminal cuttings taken at St. Malo, France, has shown that the unique features of this new Geranium are stable and reproduced true to type in successive generations of asexual reproduction.

SUMMARY OF THE INVENTION

The following traits have been repeatedly observed and are determined to be the unique characteristics of 'Guipierre'. These characteristics in combination distinguish 'Guipierre' as a new and distinct cultivar:

1. Upright plant habit.
2. Moderately vigorous growth habit.
3. Zoned dark green leaves.
4. Numerous long-lasting dark purplish red-colored semi-double to double flowers.
5. Basal branching; high yield of cuttings.
6. Continuous flowering throughout the summer.
7. Foliage tolerant to rain, wind and stress conditions.

Plants of the new Geranium are more freely flowering than plants of the female parent, the proprietary selection 4384.

The new Geranium can be compared to the male parent, the cultivar Jacques Cartier. However, in side-by-side comparisons conducted in St. Malo, France, plants of the new Geranium differ from plants of the cultivar Jacques Cartier in the following characteristics:

1. Plants of the new Geranium are more vigorous than plants of the cultivar Jacques Cartier.

2. Plants of the new Geranium have shinier leaves than plants of the cultivar Jacques Cartier.

3. Flowers of plants of the new Geranium last longer than flowers of plants of the cultivar Jacques Cartier.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical plant of 'Guipierre'.

The photograph on the second sheet comprises a close-up view of lower (left) and upper (right) surfaces of typical leaves of 'Guipierre'. Flower and foliage colors in the photographs may appear different from the actual colors due to light reflectance. Both the plants used in the photographs and the plants described in the detailed botanical description were about 7 to 9 weeks in age, and grown under the same environmental conditions as described below.

DETAILED BOTANICAL DESCRIPTION

The cultivar Guipierre has not been observed under all possible environmental conditions. The phenotype may vary somewhat with variations in environment such as temperature and light intensity, without, however, any variance in genotype. The following observations, measurements and comparisons describe plants grown 14-cm pots in St. Malo, France, under commercial practice in a glass-covered greenhouse with day temperatures about 20° C., night temperatures about 18° C. and light levels generally about 450 W/m$^2$. In the following description, color references are made to The Royal Horticultural Society Colour Chart except where general terms of ordinary dictionary significance are used.

Botanical classification: *Pelargonium peltatum* cultivar Guipierre.

Parentage:

*Male parent.*—*Pelargonium peltatum* cultivar Jacques Cartier, not patented.

*Female parent.*—Proprietary *Pelargonium peltatum* selection code number 4384.

Propagation:

*Type cutting.*—Terminal cuttings.

*Time to initiate roots.*—Summer: About 10 days with 20° C. Winter: About 12 days with 18° C.

*Rooting habit.*—Strong, fibrous and freely branching.

Plant description:

*General appearance.*—Upright and rounded growth habit. Typically grown in 10.5 to 15-cm containers.

*Crop time.*—Starting with a rooted cutting, about seven weeks are required to produced a finished flowering plant in 12-cm container.

*Vigor/growth rate.*—Moderately vigorous and rapid growth rate.

*Plant height* (*to top of foliage*).—About 14 to 20 cm.

*Plant width.*—About 30 cm.

*Branching habit.*—Freely branching with about six lateral branches at the base; pinching typically not required.

*Lateral branch length.*—About 10 to 14 to cm.

*Foliage description.*—Leaves simple, generally symmetrical, abundant, opposite. Length: About 5.5 to 7 cm. Width: About 7 to 9 cm. Shape: Peltate, palmately lobed. Venation: Palmate. Texture: Both surfaces pubescent. Aspect: Undulating towards margin. Durability: Leaves very tolerant to rain, wind and stress conditions. Cuttings withstand transport well. Petiole length: About 5 to 7 cm. Petiole diameter: About 2 mm. Color: Young foliage, upper surface: 137A to 147A. Young foliage, lower surface: 146B to 146C. Fully expanded foliage, upper surface: 137A to 147A with zonation pattern, 147A, about 1 cm in width and about 1 cm from margin. Fully expanded foliage, lower surface: 146B to 146C. Petiole: 144A.

Flower description:

*Flower type and habit.*—Dark purplish red-colored flowers. Freely and continuously flowering. Flowers arranged in hemispherical umbels arising from apical leaf axils. Umbels displayed above the foliage. Flowers semi-double to double and rounded. Umbels persistent. Flowers last about 2 to 3 weeks on the plant; self-cleaning. Not fragrant.

*Flowering season.*—Year-round under greenhouse conditions. In the garden, flowering is continuous from April to mid-September in the Northern Hemisphere.

*Umbels.*—Number of flowers per umbel: About 15. Diameter: About 8 to 10 cm. Height: About 4 to 5 cm.

*Flowers.*—Diameter: About 5 to 6 cm. Depth (height): About 2 to 2.5 cm.

*Flower buds.*—Length: About 1.2 to 1.5 cm. Diameter: About 5 to 7 mm. Shape: Elongated ovoid.

*Petals/petaloids.*—Quantity: About 12 petals and about two to five smaller petaloids per flower. Arrangement: Imbricate. Petal length: About 2 to 2.9 cm. Petal width: About 1 to 1.7 cm. Petaloid length: About 1.8 to 2 cm. Petaloid width: About 1 to 1.5 cm. Shape: Upper petals and petaloids: Obtuse. Lower petals: Obovate. Base: Attenuate. Margin: Entire. Texture: Smooth, velvety. Color, fully opened flowers: Upper petals, upper surface: Close to 60A to 59A; base of veins, very dark, close or darker than 59A. Upper petals, lower surface: Between 57C and 66C. Lower petals, upper surface: Close to 60A to 59A. Lower petals, lower surface: Between 57C and 66C. Petaloid color, upper surface: Close to 60A to 59A. Petaloid color, lower surface: Between 57C and 66C.

*Sepals.*—Quantity: About 5, not imbricate. Length: About 1 to 1.3 cm. Width: About 3 to 5 mm. Shape: Lanceolate. Apex: Apiculate. Margin: Entire. Color: Light green with slight purple Flush anthocyanin.

*Peduncle* (*umbel stem*).—Length: About 8 cm. Diameter: About 3 to 4 mm. Angle: Erect. Texture: Pubescent. Color: Light green with purple anthocyanin flush.

*Pedicel* (*individual flower stem*).—Length: About 1.2 to 2.5 cm. Diameter: About 2 mm. Angle: Between 45 and 90° to peduncle. Texture: Pubescent. Color: Medium to light green with reddish flush.

*Reproductive organs.*—Androecium: Quantity of stamens: About three to five. Anther size: About 2 to 3 mm. Anther color: 53A. Pollen color: 34B. Gynoecium: Quantity of pistils: One. Pistil length: About 4 mm. Style length: About 2 to 3 mm. Stigma shape: Five-parted. Stigma color: 53B. Style color: Greenish to yellow to light pink. Ovary color: Green.

Disease resistance: Resistance to pathogens common to Pelargonium has not been observed.

Seed development: Seed production has not been observed.

It is claimed:

1. A new and distinct cultivar of Geranium plant named 'Guipierre', as illustrated and described.

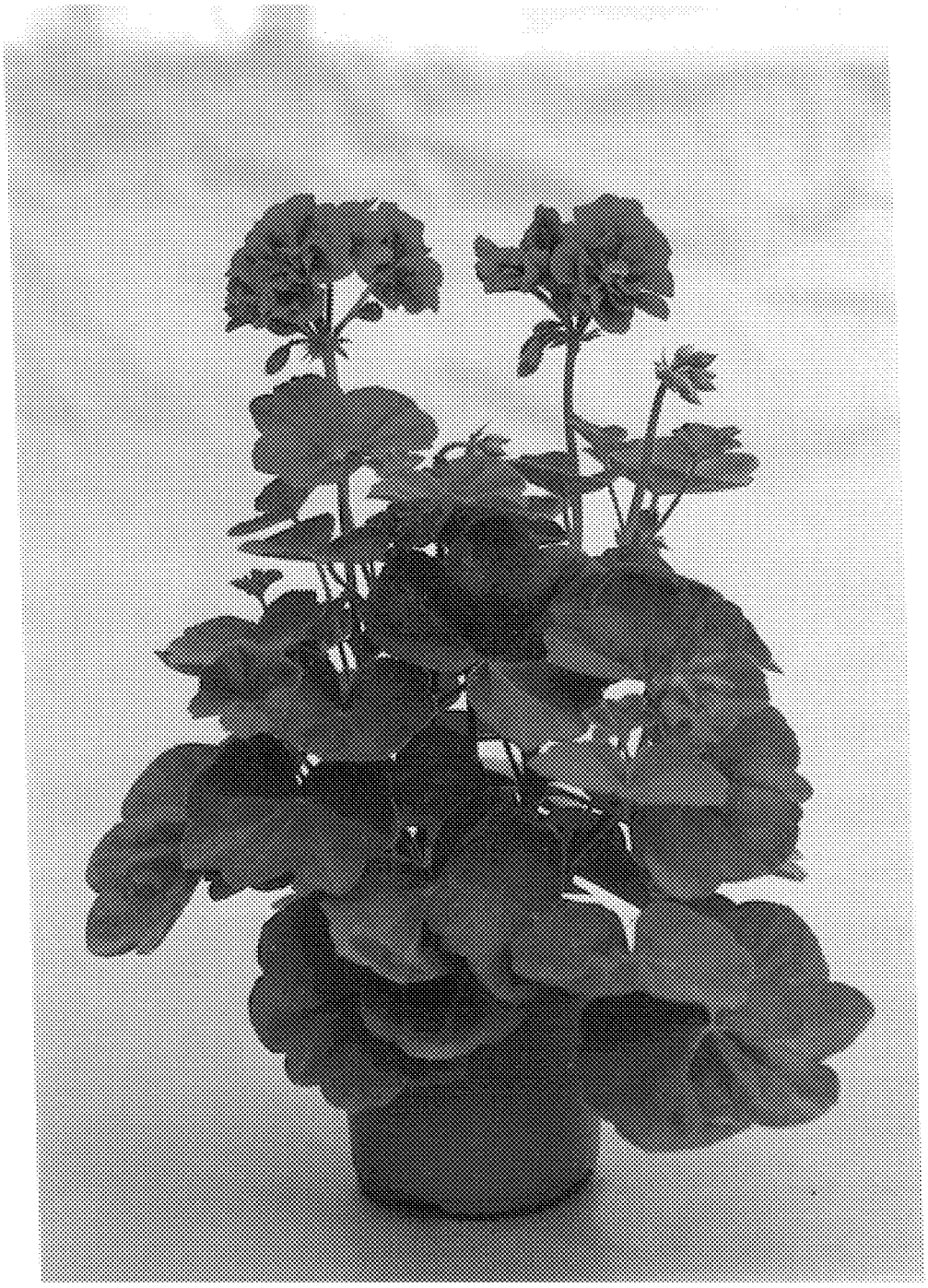

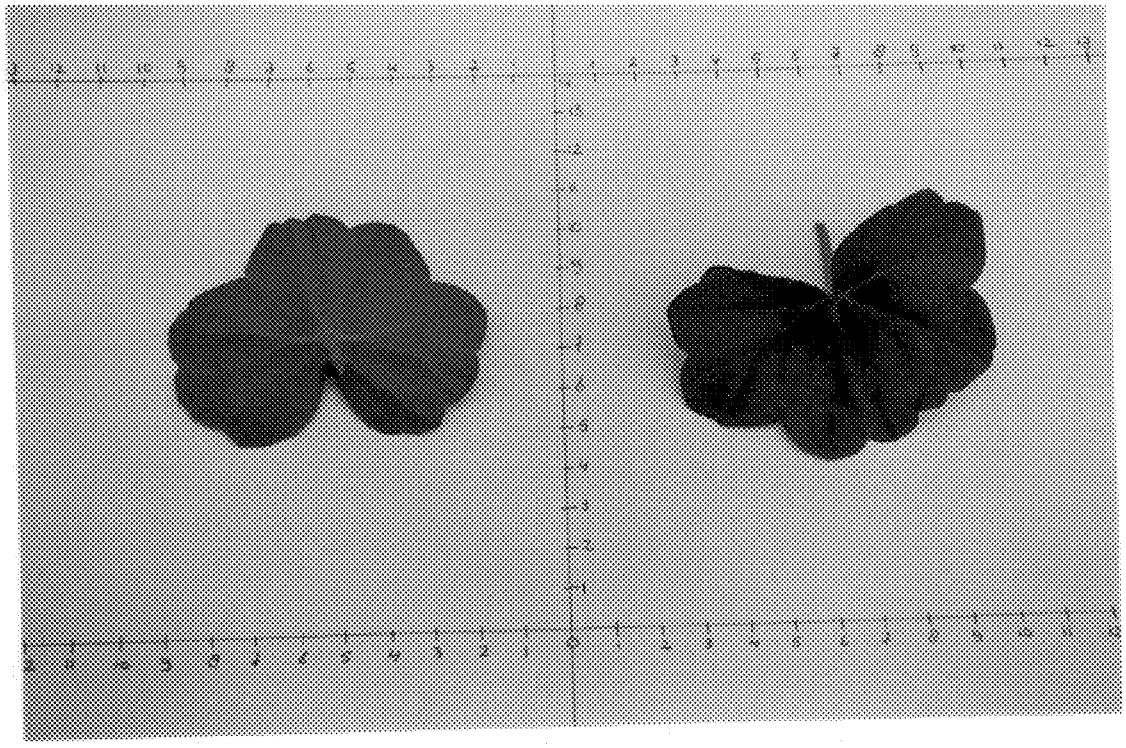

* * * * *